United States Patent [19]
Dealy

[11] Patent Number: 4,571,989
[45] Date of Patent: Feb. 25, 1986

[54] METHOD AND APPARATUS FOR MEASURING RHEOLOGICAL PROPERTIES OF FLUID

[76] Inventor: John M. Dealy, 305 Grosvenor Ave., Montreal, Canada, H3Z 2M1

[21] Appl. No.: 661,319
[22] Filed: Oct. 16, 1984
[51] Int. Cl.⁴ ............................................. G01N 11/00
[52] U.S. Cl. ......................................................... 73/60
[58] Field of Search ....................................... 73/60, 54

[56] References Cited

U.S. PATENT DOCUMENTS 3,501,948  3/1970  Spitsbergen ..................... 73/60 X
4,464,928  8/1984  Dealy ................................. 73/54

FOREIGN PATENT DOCUMENTS 56-74639  6/1981  Japan ................................... 73/60
200310   9/1967  U.S.S.R. ............................... 73/60

Primary Examiner—Stewart J. Levy
Assistant Examiner—Joseph W. Roskos
Attorney, Agent, or Firm—Robert J. Schaap; Eric Fincham

[57] ABSTRACT

There is provided a method and apparatus for measuring the viscosity and other rheological properties of a viscoelastic fluid wherein the fluid flows through a fluid channel which has a plate mounted therein, the plate having a surface which is substantially parallel to a wall surface defining the channel and the plate is moved with respect to the wall to thereby subject fluid between the wall surface and the plate to a shearing deformation, and subsequently measuring the shear stress of the fluid at the wall when subjected to the shearing deformation.

10 Claims, 4 Drawing Figures

METHOD AND APPARATUS FOR MEASURING RHEOLOGICAL PROPERTIES OF FLUID

The present invention relates to a method and apparatus for measuring the viscosity and other rheological properties of a viscoelastic fluid.

In certain industries, such as the plastics industry, it is often desirable to be able to determine rheological properties of the molten plastic at a certain point in a process. This point might be the outlet of a polymerization reactor, a blending or compounding device, an extruder, or some other known device. Many reasons exist for knowing the rheological properties and in a particular process, the measurement of rheological properties could be used as an input signal for a closed loop control system or simply to monitor product quality.

Process rheometers are commercially available and are used for molten plastics. Mainly such process rheometers are of the "on-line" type in which a sample side stream is drawn from the main process flow by a gear pump that produces a controlled flow rate through the rheometer. Typical of disadvantages are long delay times, complexity, high cost, and the inability to determine non-linear viscoelastic characteristics. It is also known in the art to carry out "in-line" viscosity measurement by measuring pressure drop through a tubular section of the main process flow (if the flow rate is known). Disadvantages of this type of instrumentation include problems due to generally large pressure fluctuation in process lines and the fact that the true viscosity cannot be determined because the true shear rate at the wall is unknown. Furthermore, no information about melt elasticity can be obtained.

For Newtonian fluids, the viscosity is sometimes monitored by measuring the drag force exerted by the flowing fluid on a blade or other obstruction in the flow passage. This method, however, is not suitable for non-Newtonian fluids because the viscosity depends on the local value of the shear rate and this varies greatly in the neighborhood of the obstruction.

It is therefore an object of the present invention to provide a flow-through rheometer for measuring rheological properties in a viscous or viscoelastic fluid.

It is a further object of the present invention to provide a method for measuring rheological properties in a flowing viscous or viscoelastic fluid from which may be determined certain viscoelastic properties of the fluid.

According to the invention, there is provided a device for measuring rheological properties of a fluid, the device including a fluid channel having a wall at least partially defining the channel thereabout, a plate mounted in the fluid channel, the plate having a surface substantially parallel to at least a portion of the wall, means for moving the plate such that the surface moves with respect to the wall in a direction parallel to that wall to thereby subject a fluid between the wall and surface to a shearing deformation, and means for measuring the shear stress of the fluid when subjected to the shearing deformation.

The invention also includes the method of measuring rheological properties of a fluid comprising the steps of providing a fluid channel defined by at least one wall and having a movable plate therein with one surface mounted substantially parallel to a portion of the wall, moving the plate to thereby cause the fluid between the surface and wall to be subjected to a shearing deformation, and measuring the shear stress of the fluid while subjected to the shearing deformation.

In greater detail, the fluid flows through a channel in which there is provided a movable shearing surface parallel to one wall of the channel and which surface preferably offers a minimal obstruction to the main flow. The channel may be any suitable one and included within the scope of this invention is any device adapted to contain the fluid. The movable shearing surface is linked to means to cause the surface to move with respect to the wall (either linearly or rotationally) so as to subject the fluid in the shearing gap between the shearing surface and nearby wall to a shearing deformation or a close approximation thereof.

The determination of rheological properties requires that the shear stress be known in addition to the shear strain or shear rate. However, measurement of the total force on the shearing plate (in the case of linear motion) or the total torque (in the case of rotary motion) will not suffice for this purpose as these quantities include contributions from (1) shear stress in the fluid on the other side of the shearing surface; (2) material around the edges that has not been ideally deformed; and (3) forces due to friction in the seals for the mechanism that moves the shearing surface. To overcome this, the shear stress should be measured over a small area and a suitable mechanism is the shear stress transducer shown in U.S. Pat. No. 4,464,928, issued Aug. 14, 1984 to John Dealy, the teachings of which are incorporated herein by reference.

If the motion of the shearing surface is steady over a significant period of time, then the viscosity can be determined as the ratio of the shear stress to the shear rate. If the shearing surface is made to oscillate sinusoidally, then measurement of the shear stress as a function of time permits calculation of the storage and loss moduli by use of standard formuli. Many other useful rheological material functions can also be measured, such as stress relaxation after the cessation of the steady shearing at a high rate. Thus, one could program many linear or angular displacements of the shearing surfaoe to generat desired histories.

The shearing gap should be as small as possible to ensure that the shear strain and shear rate are uniform across the gap. However, this gap should be maintained at a fixed value so that the instrument calibration will not change. The shear strain is given by x/h, where x is the displacement of the shearing plate relative to the wall and h is the gap. For example, if h is 0.80 mm and the plate is displaced through a distance of 1 cm, the shear strain is (10.0 mm/0.8 mm)=12.5 strain units. A preferred range of gap is from 0.5 to 2.5 mm although a wider gap would be suitable for viscosity determination, since the plate displacement speed would be constant over a significant period of time. However, for the use of transient tests to determine viscoelastic properties, the gap should be as small as possible.

As previously mentioned, U.S. Pat. No. 4,464,928 teaches a shear stress transducer which can be mounted in the wall surface. The shear sensitive surface of the transducer should be small compared to the shearing plate so that during measurements, this surface does not get closer to the edge of the plate than 5h. For example, if h is 1.0 mm, the shear sensitive surface preferably should not come closer than 5 mm to the edge of the shearing plate. This is because the flow near the edge of the plate may not be uniform and will be influenced by the edge.

In the case of a shearing plate that rotates about a fixed axis, the shear rate at a distance R from this axis is $$\dot{\gamma} = \frac{R}{h} \frac{d\theta}{dt}$$

where $\theta$ is the angular displacement of the plate in radians. When the fluid involved is non-Newtonian, it is important that the shear rate variation over the area of the shear sensitive surface be kept small. For example, if the width of this surface, measured in the direction of a radius from the axis of rotation, is 5% of the average value of R over this width, then the variation of shear rate across the shear sensitive surface will be about 5%.

Having thus generally described the invention, reference will be made to the accompanying drawings illustrating embodiments thereof, in which.

Figure 1:
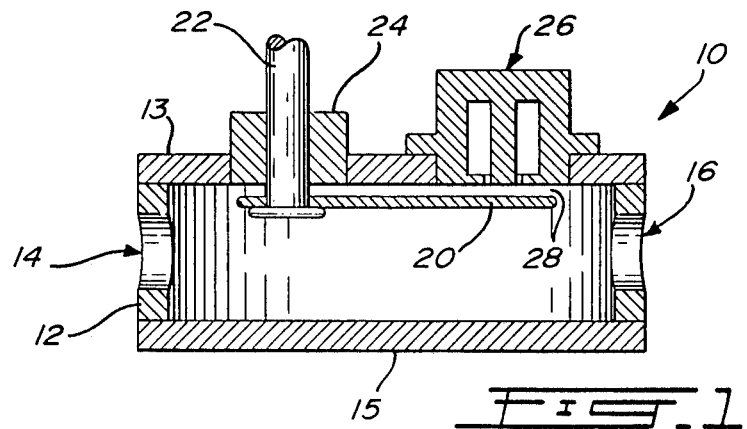
FIG. 1 is a cross-sectional view of one embodiment of a rheometer according to the present invention.
Figure 2:
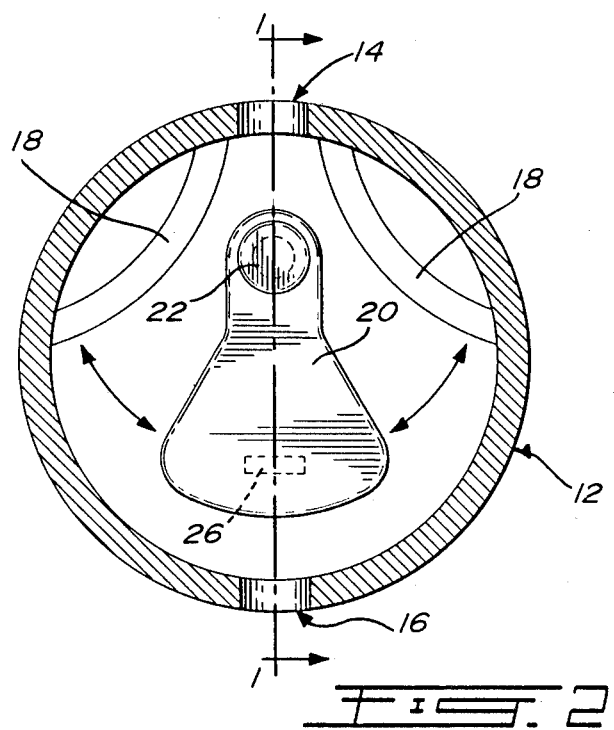
FIG. 2 is a bottom view of the rheometer of FIG. 1 with the bottom plate removed.
Figure 3:
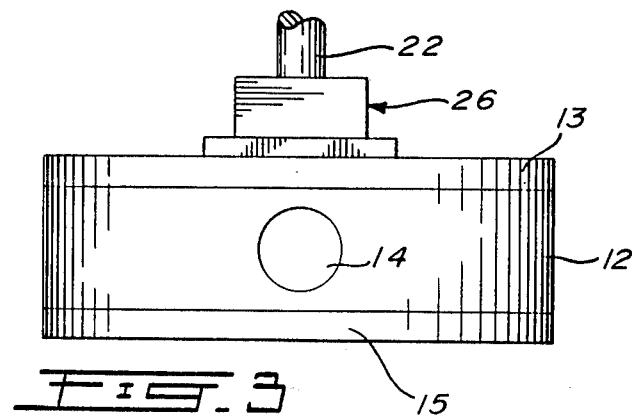
FIG. 3 is a sectional view taken along the lines A—A of FIG. 2.

Referring to the drawings in greater detail and by reference characters thereto, the rheometer of the embodiment illustrated in FIGS. 1 to 3 is generally designed by reference numeral 10. Rheometer 10 of an overall cylindrical configuration, has an inlet 14 and an outlet 16 formed in cylindrical wall 12 which is bounded by upper wall 13 and bottom wall 15. Interiorly of the rheometer, there are provided arcuate sections generally designated by reference numeral 18; arcuate sections 18 are utilized to streamline the flow within the rheometer and prevent stagnant zones.

Rheometer 10 includes a shearing plate 20 mounted on a shaft 22 which passes through a suitable bearing seal 24. In turn, shaft 22 is connected to a suitable rotary actuator (not shown). As may be seen from FIG. 2, shearing plate 20 is mounted close to upper wall 13 to provide a small shearing gap 28 between the wall and its upper surface.

The apparatus includes a shear stress measuring device generally designated by reference numeral 26. Device 26 is mounted in upper wall 13 on the center line of the rheometer where its shear sensitive surface will "see" shearing plate 20 over its maximum angular deflection (indicated by arrows in FIG. 2). Device 26 may be one similar to that taught in U.S. Pat. No. 4,464,928 issued Aug. 14, 1984 to John Dealy. The flow through the shearing gap between shearing plate 20 and upper wall 13 may be driven by the pressure gradient of the main process flow. Alternatively, the rheometer could be used in an "on-line" configuration by using a gear pump to draw a sample stream from the main flow and pump it through the rheometer.

Although the pressure driven flow through shearing gap 28 will affect the shear rate somewhat, if the gap is small compared to the total channel height, then this flow will be quite small. If, under certain situations, this poses a disadvantage from the point of view of fluid residence time, the shearing plate 28 can be periodically moved far to one side to permit fresh fluid to flow into the gap region.

Figure 4:
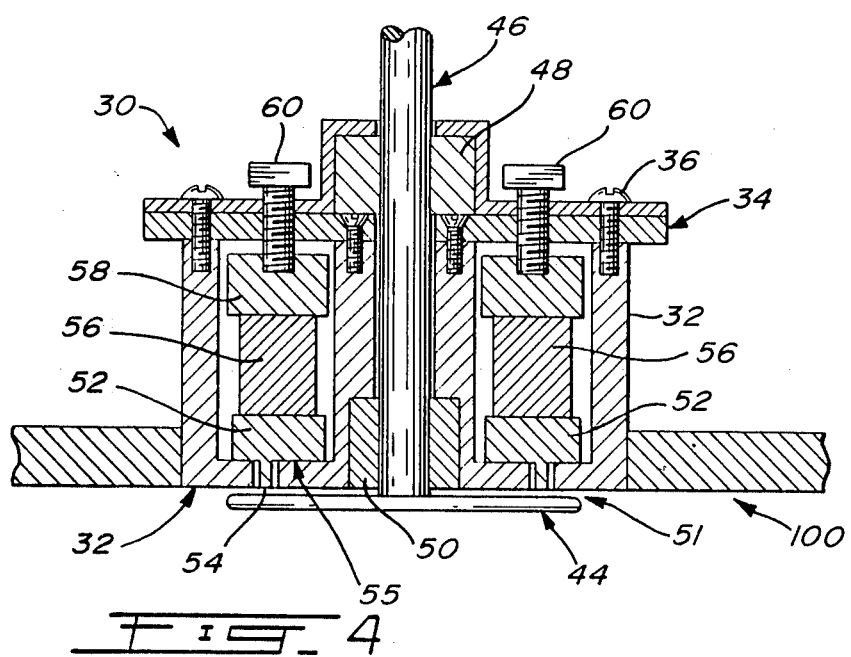
FIG. 4 is a cross-sectional view of a further embodiment of a rheometer comprising a self-contained module.

In a second embodiment of the invention, illustrated in FIG. 4, there is provided a self-contained module generally designated by reference numeral 30 which is designed to be mounted flush with a flat surface 100 past which the fluid of interest is flowing under the influence of a pressure gradient. The apparatus includes an exterior wall housing 32 having a cover 34 attached to housing 32 by means of screws 36.

Rheometer 30 includes a shearing plate 44 mounted on shaft 46 around which is provided bearings 48 and 50 which keep the rotor shaft properly centered during operation. Shaft 46 is connected to a suitable rotary actuator or speed control motor (not shown) so that various shear rates or shearing patterns can be generated in shearing gap 51.

A shear sensitive surface 54 is an annular protrusion on a torque transmitter 52. The torque generated is sensed by a piezoelectric crystal 56 which is held in a state of compression between torque transmitter 52 and a compression washer 58. The compressive stress on the piezoelectric crystal 56 can be adjusted by means of machine screws 60.

In this embodiment, elastomeric gasket 55 is compressed between torque transmitter 52 and the inner wall of the face of the rheometer and thus prevents the flow of fluid into the rheometer. Since piezoelectric devices have an extremely low compliance, the resistance offered by the gasket to the torsional deflection of the torque transmitter and thus to the response of the crystal to the applied shear stress will not introduce serious errors. In any event, it can be taken into account by calibrating the crystal while mounted in the rheometer with the gasket in place. As in the case of the previous embodiment, the flow through the shearing gap by the pressure gradient of the main flow is relatively small because the gap is small. The rheometer, as previously discussed, can be mounted in the wall of a flow chamber fed by a gear pump so that "on-line" rather than "in-line" operation is possible.

It will be understood that the above-described embodiments are for purposes of illustration only and that changes and modifications may be made thereto without departing from the spirit and scope of the invention.

I claim:

1. An apparatus for measuring rheological properties of a fluid comprising a fluid channel having a wall at least partially defining the channel, a plate mounted in said fluid channel, said plate having a surface substantially parallel to at least a portion of said wall, means for moving the plate such that the plate surface moves with respect to the wall to thereby subject fluid between the wall and surface to a shearing deformation, a shear stress transducer mounted in said wall where said fluid is subjected to said shearing deformation, said transducer having a member adapted to measure the tangential force exerted thereon by said fluid 2. The apparatus of claim 1 wherein said means for moving the plate comprises means for moving the surface rotationally with respect to said wall.

3. The apparatus of claim 1 wherein said means for moving the plate comprises means for moving the surface linearly with respect to said wall.

4. The apparatus of claim 1 wherein said shear stress transducer has a measurement area for measuring shear stress substantially smaller than the surface area of said movable plate.

5. The apparatus of claim 1 wherein the distance between said plate surface and said wall is between 0.5 mm to about 2.5 mm.

6. The apparatus of claim 1 wherein said means for measuring the shear stress comprises a shear sensitive surface of a torque transmitter and a piezoelectric crystal adapted to sense torque transmitted by said torque transmitter and means for holding said piezoelectric crystal in a state of compression.

7. A method of measuring rheological properties of a fluid comprising the steps of providing a fluid channel defined by at least one wall and having a movable plate therein with one surface of said plate mounted substantially parallel to a portion of the wall, moving the plate to thereby cause a fluid between the surface and wall to be subjected to a shearing deformation, and measuring the shear stress exerted by the fluid on the wall or the plate over an area that is small compared to the surface area of said movable plate while the fluid is subjected to the shearing deformation.

8. The method of claim 7 wherein said fluid comprises a viscous or viscoelastic fluid.

9. The method of claim 8 wherein the step of moving the plate comprises the step of moving the plate linearly with respect to said wall.

10. The method of claim 8 wherein the step of moving the plate comprises the step of moving the plate rotationally with respect to said wall.

* * * * *